United States Patent [19]

Auerbach et al.

[11] 4,096,865

[45] Jun. 27, 1978

[54] METHOD AND APPARATUS FOR MONITORING A TIMED FAILURE CONDITION RELATIONSHIP IN A CARDIAC PACER

[75] Inventors: Albert A. Auerbach, New York; Sidney Steinberg, Spring Valley, both of N.Y.

[73] Assignee: Medalert Corporation, New York, N.Y.

[21] Appl. No.: 664,952

[22] Filed: Mar. 8, 1976

[51] Int. Cl.² ............................................. A61N 1/36
[52] U.S. Cl. ............................................. 128/419 PT
[58] Field of Search ............... 128/2.06 A, 2.06 R, 128/419 PT, 419 PG

[56] References Cited

U.S. PATENT DOCUMENTS

| 3,651,799 | 3/1972 | Daynard | 128/419 PT |
|---|---|---|---|
| 3,662,759 | 5/1972 | Daybolt | 128/419 PT |
| 3,669,120 | 6/1972 | Nielsen | 128/419 PG |
| 3,703,900 | 11/1972 | Holznagel | 128/419 PG |
| 3,742,938 | 7/1973 | Stern | 128/419 PT |
| 3,756,246 | 9/1973 | Thaler et al. | 128/419 PT |
| 3,782,367 | 1/1974 | Hochberg et al. | 128/419 PT |
| 3,833,005 | 9/1974 | Wingrove | 128/419 PG |
| 3,920,024 | 11/1975 | Bowers | 128/419 PG |
| 3,949,758 | 4/1976 | Jirax | 128/419 PT |

Primary Examiner—William E. Kamm
Attorney, Agent, or Firm—S. C. Yuter

[57] ABSTRACT

A pacer for cardiac pacing and condition monitoring in which the electrical characteristics of the pacer are altered upon a temporary or permanent change in monitored conditions, such as the failures defined as a "loss of capture" or a "failure to sense", in which the timed relationship between the pacer signal generator and the cardiac signal is monitored to indicate detection of failure condition. The monitor acts to provide both increased stimulus to recover capture and to provide warning pulses indicating loss of capture or failure to sense, which are sufficiently discernible upon an electrocardiogram to enable later diagnosis, even after self-correction. After diagnosis, the monitor can be reset to its original condition by means of an external control, such as a magnet. The unit may be surgically implanted or employed externally. Remote or patient operated local failure detectors can be employed with the pacer to automatically detect, indicate, and provide an alarm if any prior intermittent sensing or capture failure occurred.

7 Claims, 10 Drawing Figures

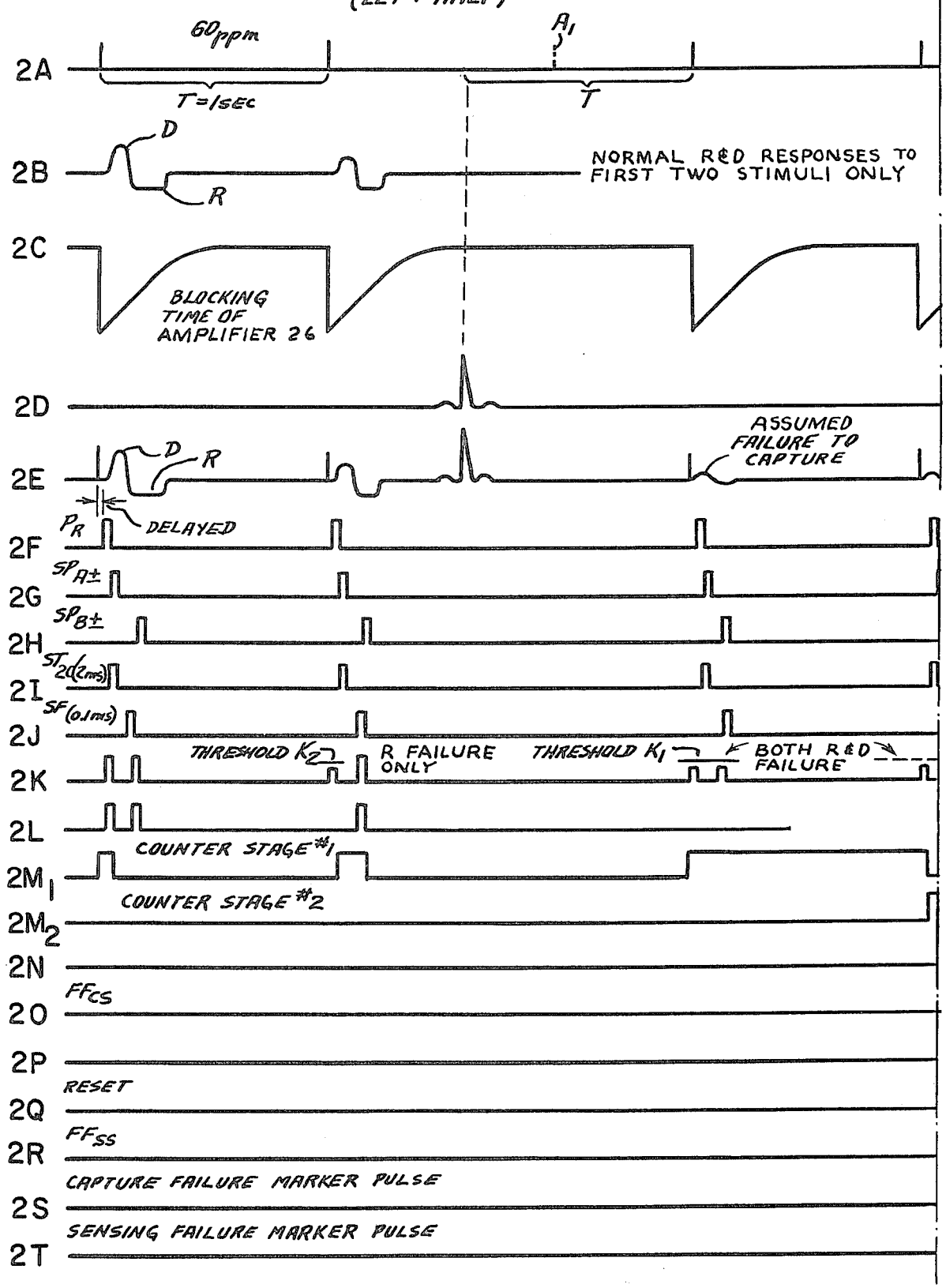

(RIGHT HALF)

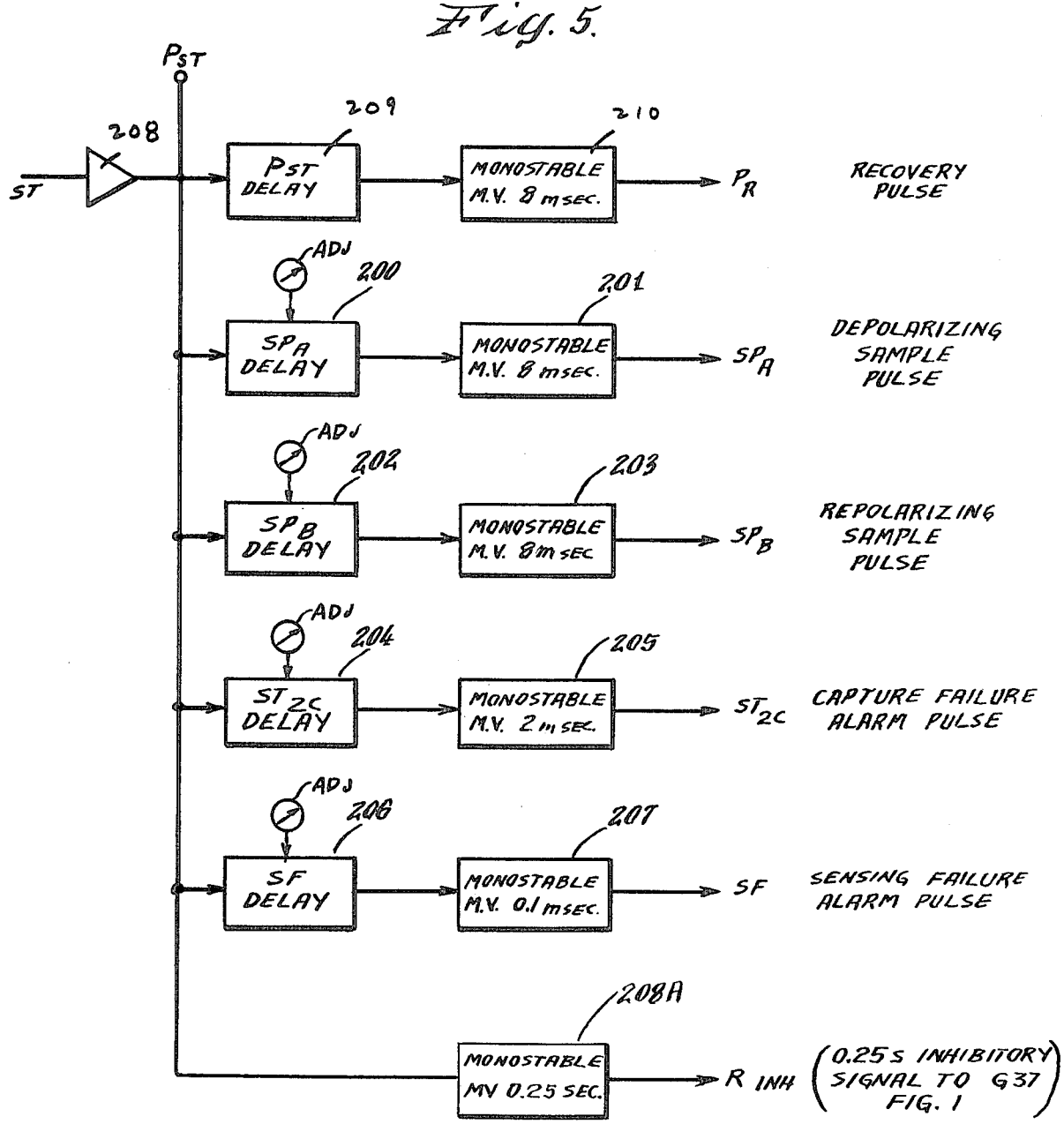

METHOD AND APPARATUS FOR MONITORING A TIMED FAILURE CONDITION RELATIONSHIP IN A CARDIAC PACER

This invention relates to cardiac pacers, and more particularly to monitoring equipment employed for use in conjunction with, and as a component of cardiac pacer mechanisms for detecting the occurrence of certain failure conditions.

As is well known, the function of a cardiac pacer is to provide an appropriate stimulus to the heart. The stimulus is applied to the heart by placement of an appropriate wire or electrode in an appropriate region of the heart. In the operation of such devices, it is extremely important that the electrode maintain its proper contact with the heart tissue in order to insure that the stimulus is both properly applied and received. In the course of normal operation, however, it is not uncommon for the electrode to shift, or to develop a reticulum of connective fibers or the like between the electrode and the heart tissue, and thus diminish the effective amplitude of the stimulus. Further, it is not uncommon for electronic problems to occur. Both of these effects give rise to "loss of capture," a condition which prevents the applied signal from adequately stimulating the heart.

The most commmon type of cardiac pacer employed today is the so-called demand type pacer. In a demand pacer, the circuitry includes provision for stimulus inhibition by spontaneous activity of the heart. This is required because a stimulus which occurs in the presence of spontaneous activity may, under certain conditions, induce a persistent and dangerous ventricular fibrillation which prevents adequate blood circulation. The pacer senses this spontaneous activity and inhibits the production of artificially generated stimuli. Another cause of danger in such operations is the failure of the unit to sense such activity in a manner producing the inhibition of the generating signal.

In addition to the elimination of the foregoing conditions, it is also desirable to provide a permanent indication (which will be visible on an EKG trace) to enable the physician examining the EKG record to detect that there had been a prior intermittent failure of the pacer, which may no longer be occurring, at the time the EKG trace was taken. This is accomplished by placing some form of permanent indication on the EKG signal which is otherwise not a part of the normal recorded signal and yet would be evident to the EKG operator.

Prior systems for monitoring pacer operations are known, such as, for example, disclosed in the patent to Howard Martin Hochberg and Eugene King, U.S. Pat. No. 3,782,367, issued Jan. 1, 1974. In such prior devices, it is conventional to monitor the pacer by means of external equipment detecting the various operations of the pacer functions. Since such equipment is external to the patient, the patient can use this equipment only under hospital or clinical conditions. There is moreover, no possibility of modifying the EKG to indicate a prior intermittent failure. However, it is desirable to provide a completely self-contained unit within the implanted pacer which will contain all of the monitoring and storage equipment necessary to both detect a pacer malfunction of the various types noted above, and in addition, to take corrective action in instances where such failures, as are described above, have occurred, and finally mark the EKG with an indicator signalling the prior occurrence of the malfunction.

In accordance with the invention described in the aforesaid application Ser. No. 578,644, an autodiagnostic, self-contained, implantable cardiac pacer is provided. This unit is also available as an external pacer used in the clinic.

It is the object of the present invention to provide an improvement to the aforesaid electronic system wherein an additional method and apparatus for detecting sensing failures is used in a solid state self-contained unit which can be coupled to any existing electrode system (bipolar or unipolar), and which may be used in an implantable or temporary (external) pacer.

The foregoing object is achieved by a self-checking circuit which looks for the absence of "recycling" of the pacemaker timing circuit following the occurrence of a spontaneous cardiac signal. This condition indicates a "sensing failure."

In conventional pacers, the pacer is refractory, after the stimulation signal is applied, for a period of time which normally encompasses the response evoked by that stimulation signal. By "refractory" is meant that the pacer signal amplifiers are blocked by the relatively large (i.e., with respect to the measured response) stimulation signal. To counteract this effect, and to provide means for measuring and sampling the depolarization and/or repolarization characteristics of the cardiac response signal, the invention, as described in the aforesaid copending applicaton, provides for amplification and detection components which are coupled to fast recovery means for unblocking these amplifiers as soon as possible. Of course, the amplifiers may be made of components which themselves undergo a very rapid unblocking, at least sufficient to enable the sampling of the response signals. Once this unblocking condition has been achieved, then a means for sensing the cardiac response to the stimulation signal may be provided. The depolarization or repolarization, or both, components of the cardiac response may be separately measured by this sampling technique. The sampled portions of these cardiac responses are then compared to a predetermined threshold level which is set in accordance with the desired level of response which is considered satisfactory. A monitoring device is provided for counting the number of consecutive times the threshold is not exceeded, consecutively, and providing an alarm when such predetermined number of times is achieved. For example, if a three failure limit is set, then upon the fourth failure a second signal will be generated by the monitoring device which will have two effects. The first effect will be to provide an increased magnitude stimulation signal to the electrodes. It has been found that since loss of capture may, for a variety of reasons, result from reduction in the magnitude of the effective stimulating current, increasing the magnitude of the stimulation signal is often sufficient to cause recapture. At the same time, the occurrence of paired signals indicates that a warning signal has been applied, by the stimulus generator, the warning signal having a given time relation to the increased magnitude stimulation signal. In a simple variation of this procedure, the original stimulus amplitude is left unchanged and the second paired signal, separated in time from the first and later than the first, is sufficiently large to stimulate. The warning signal in this case occurs first in time. The time separation between the warning signal and the stimulation signal is sufficient to enable the pair of signals to be read on an EKG trace. As a result, the occurrence of loss of capture is permanently recorded by the cardiac pacer at the same time that capture is resumed as a consequence of the increased magnitude stimulation signal. Thus, a physician who may eventually examine the EKG recording, will know from his recognition of the paired signals that loss of capture has occurred. He can then initiate corrective procedures after the patient has been brought back to the hospital. The monitoring unit could then be reset by means of an externally applied mechanism, such as an RF generator which will actuate detection and switch actuation elements in the pacemaker. The condition which gave rise of loss of capture can then be safely examined.

Sensing failures during the demand operating mode may be also detected by the autodiagnostic pacer. As noted previously, in such pacers, the next stimulation signal is released at the end of an "escape interval" (which is initiated by the previous stimulation signal) unless a premature ventricular contraction or a conducted (natural) heart beat (or in general, spontaneous as distinct from stimulus-evoked cardiac activity) occurs within this escape interval. To detect a sensing failure, it is necessary to provide a means for detecting the presence of a stimulation signal within a predetermined time limit after any spontaneous activity as defined above. The presence of such a stimulation signal within this interval indicates that the stimulus inhibition portion of the demand pacer is inoperative. The circuits detecting this condition are also designed to place a marker pulse into the output pulse generating circuit of the pacer, thereby placing a second timed warning pulse, giving a total of three pulses, on the EKG. Again, the marker pulse indicating sensing failure is "spaced" in time from the stimulating pulse and from the loss of capture warning signal so as to provide the EKG analyst with a visual indication that such an event had occurred. Neither the loss of capture warning signal nor the sensing failure warning signal are designed to be of sufficient duration or amplitude as to cause a stimulating effect in and of themselves, these pulses being intended to be merely marker pulses. Nevertheless, the loss of capture warning signal as noted above can also be used to stimulate, and under certain conditions, may be a more effective stimulus since its action can be "facilitated" by the occurrence of the first stimulus.

In accordance with the present improvement invention, it is recognized that an essential property of the pacer pulse generator and timer is its relationship to any spontaneous cardiac activity, herein defined as the R-wave. Since such spontaneous cardiac activity, or R-wave, must recycle the timer, a voltage change within the timer must be observed in a specific time relation to the R-wave.

If this voltage change does not occur, a sensing failure must follow. A logic circuit for timing this voltage change can thus provide an indication of such sensing failure.

The foregoing brief description of the present invention as well as the objects and advantages thereof, will become more apparent from the following more detailed description and additional advantages and objects inherent therein, and wherein:

FIG. 5 is a block diagram indicating the generation of timing signals employed in conjunction with the embodiments illustrated in FIGS. 1-3;

Figure 1:
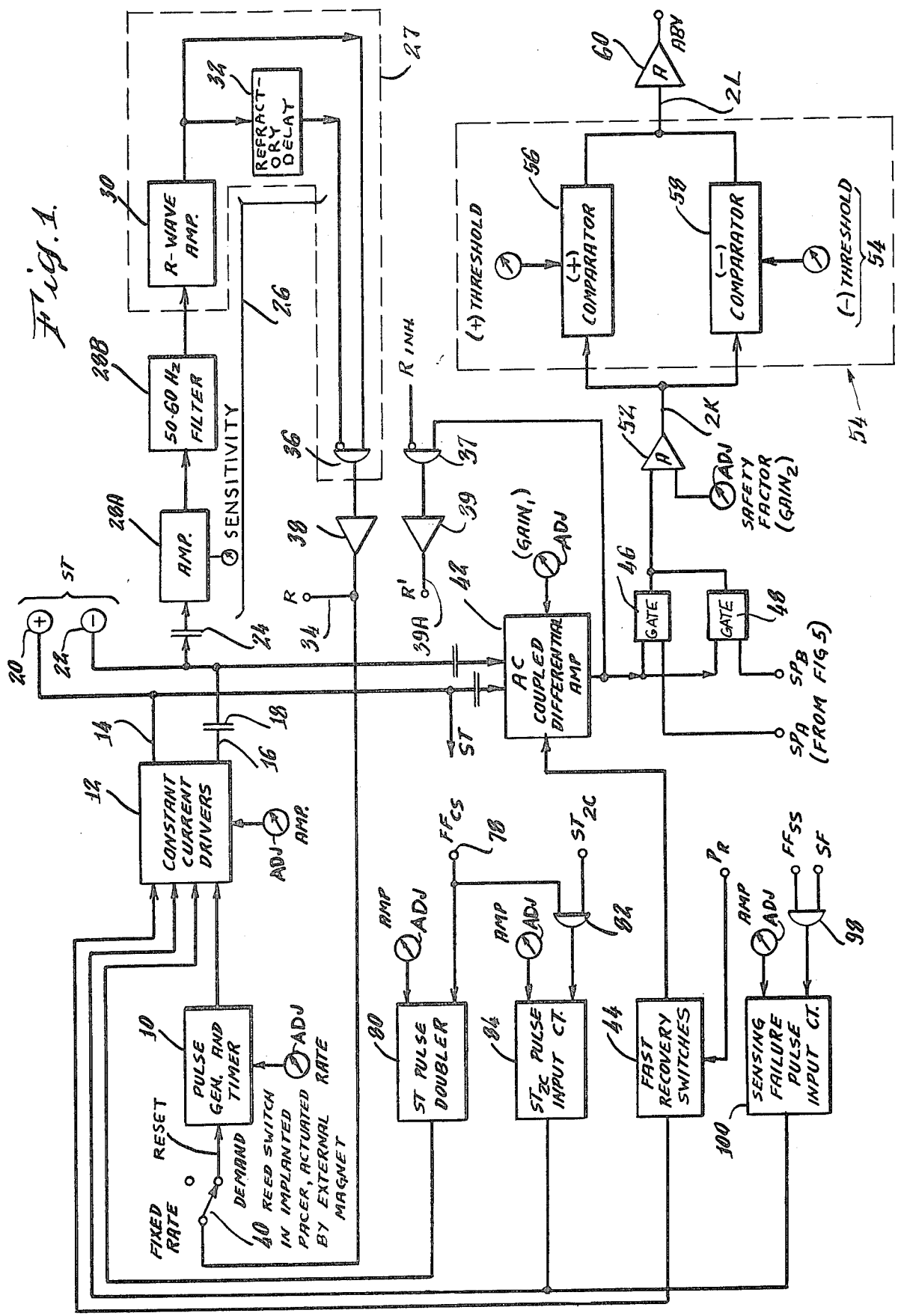
FIG. 1 is a general block diagram of a system for use with the present invention.

Referring to FIGS. 1-5, there is illustrated the system described in the aforesaid copending application Ser. No. 578,644. Thus, in FIG. 1, there is illustrated a cardiac pacer of the demand variety, employing a pulse generator and timer 10. In implanted units, the pulse generation rate is preset and fixed in accordance with a desired ("intrinsic") rate. A variable rate control may also be employed in external (temporary) pacers. The output of the generator is coupled to a constant current driver 12 which provides a current pulse of about 1 millisecond duration, between its output lines 14 and 16. The current pulse is used to initiate a contraction (i.e., stimulate) the ventricles of the heart. The possibly dangerous D.C. component of this pulse is isolated from the heart by means of the capacitor 18. The current path defined by the lines 14 and 16 is terminated in an electrode whose positive and negative terminals are labeled 20 and 22, respectively. The electrode is placed in contact with the heart tissue in a conventional manner. Current flow between the two terminals through adjacent cardiac tissue constitutes the stimulus which initiates a general ventricular contraction. The negative terminal is usually the site at which the contraction begins. Stimulating current then returns to the positive terminal. The electrode is "bipolar" if the terminals 20 and 22 are part of the same structure. If terminal 20 is the external shell of the pacer itself, the electrode is "unipolar" and the electrode structure has only terminal 22. In either case there is only a single current path from terminal 22 via cardiac tissue back to the pacer.

Figure 2:
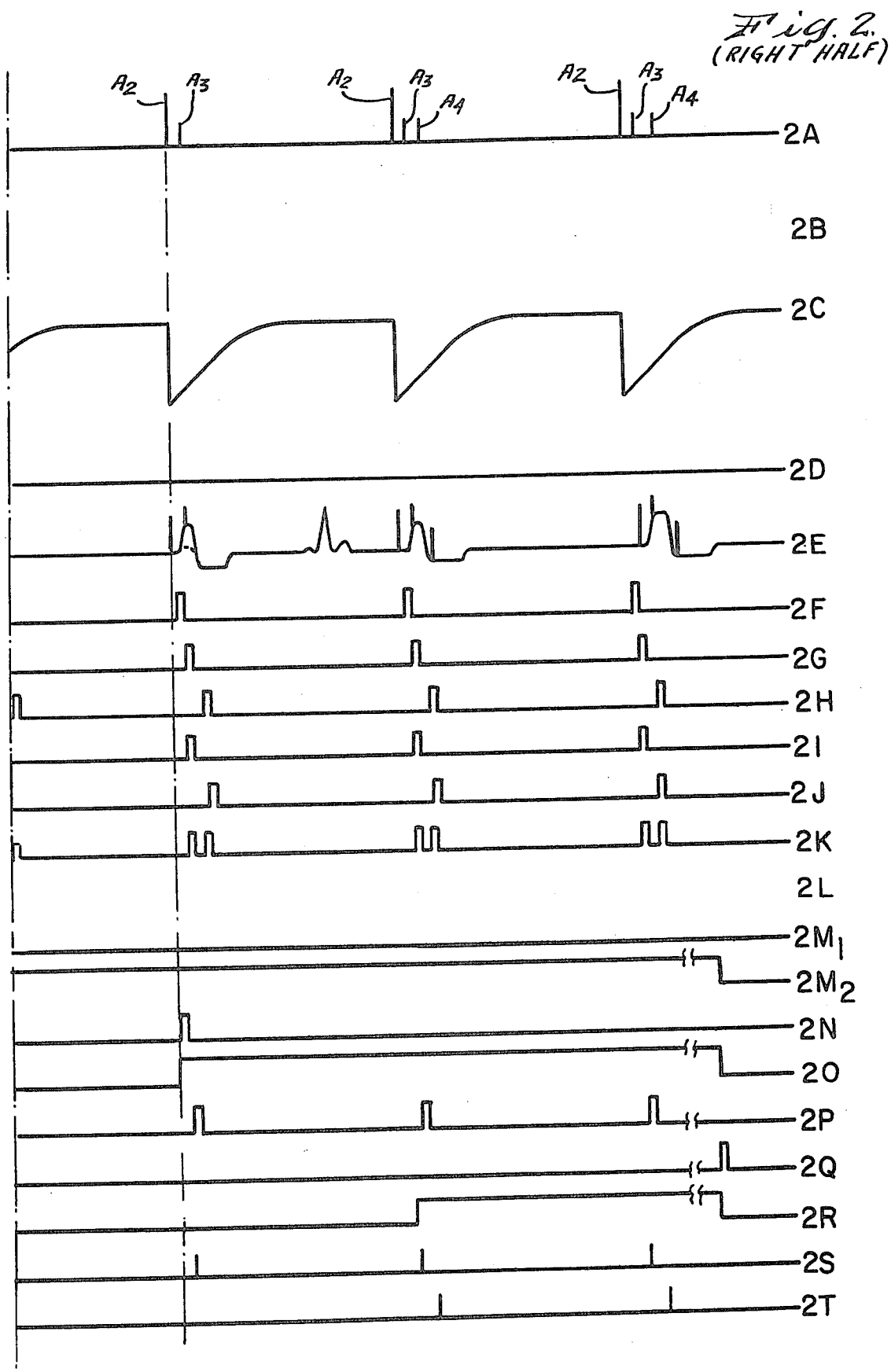
FIG. 2 is a timing diagram illustrating the relationships between the various signals employed within the system of FIG. 1.

In the demand cardiac pacer indicated, the occurrence of spontaneous (nonstimulated) cardiac activity will suppress the release of any pacer output stimuli providing that the rate of occurrence of such activity exceeds the intrinsic rate. Spontaneous activity may be supraventricular in origin, in which case the heart's natural (atrial) pacemaker initiates a train of events resulting in ventricular contractions and consequent electrical activity known as the "QRS complex" (an R-wave). Irritable cardiac tissue in the ventricle may also "twitch" spontaneously and evoke electrical currents (also producing an R-wave). In either case, the spontaneous activity inhibits stimulus release for a time period T, (which is the reciprocal of the intrinsic rate), following the spontaneous activity. The inhibition occurs by resetting ("recycling") the pulse generator-timer 10. As shown in FIG. 1, the initial stimulus signal from the driver 12 is coupled to excitable cardiac tissue via isolation capacitor 18 (FIG. 2, line 2-A). The response evoked by the stimulus (FIG. 2, line 2-B) appears across the single current path between electrode terminals 20 and 22 through capacitance 24 and is amplified by signal amplifier 28A. Ambient 50 or 60 cps electromagnetic noise may also be picked up by amplifier 28A.

Such noise is filtered out by filter 28B. The filtered output is further amplified and shaped by R-wave amplifier 30. Elements 28A, 28B, 30 and 32 constitute a functional amplifying system 26. Element 32 is a refractory delay component. It will be understood that the delay component 32 is actually the time factor required for the amplifier system 26 to recover after being stimulated by the initial stimulus pulse. Elements 30, 32 and 36 together from the component R-wave amplification 27.

The logical effect of such a saturation phenomenon is to inhibit gate 36, for the duration of the saturation period. Thus, in a normal demand pacer, both the response evoked by the stimulus (FIG. 2, line 2-A) as well as any spontaneous activity which may occur, will not be detected by the block 27 during the saturation or recovery period. Following the termination of this period, any spontaneous cardiac activity will be detected, amplified, appear at the input of gate 36 and at the output of amplifiers 38 and 30. If such activity occurs, the timing element 10 is "recycled" (i.e., reset) through optional switch 40, and the subsequent stimulus (FIG. 2, line 2-A) will be released only at the end of an interval (T) following the instant at which recycling occurs. Thus, if the heart begins to beat naturally with a rate of at least 1/T, the generator 10 will be continuously reset and the pacer remains inactive.

The pacer configuration also permits fixed pacing merely by resetting the synchronous switch 40 to the FIXED RATE position, thereby opening the loop and interrupting the feedback. In this mode, the pacer will operate at a fixed rate, continuously, until disabled.

Switch 40 is used only in external pacers. In demand pacers, the recycling output of amplifier 38 is directly connected to element 10 (and the switch is replaced by a magnetically actuated reed).

In a system such as described above, any failure of the pacer to properly stimulate the heart ("loss of capture") or failure to sense spontaneous activity and properly recycle the pacer timing circuits ("sensing failure") will not prevent continued malfunction. If sensing failure occurs, the pacer is never recycled and it thus continues to stimulate at its fixed, intrinsic rate. This condition is potentially dangerous and may initiate ventricular fibrillation in a recently infarcted heart. If loss of capture occurs, the stimuli are ineffective. Then, if there is no underlying or independent cardiac rhythm because of various conditions generically known as "heart blocks", the heart beats at its "idioventricular" rate, which may be too low a rate to sustain adequate blood circulation. Pacers, heretofore, have not been designed to be "aware" of the occurrence of such potentially dangerous events, take corrective action if they do indeed occur, and simultaneously warn an attending doctor of the occurrence of these events.

The essential requirement for detection of "loss of capture" or "sensing failure" is the ability to detect the response of the heart (FIG. 2, line 2-B) to the pacer output stimulus (FIG. 2, line 2-A). This response is normally not seen because it occurs within 15 to 50 millisecond after the stimulus, i.e., within the saturation or recovery period of the conventional amplifying system 26 and 27. Therefore, to make this response "visible", an additional compensated A.C. coupled differential amplifier 42 is capacitively coupled to electrode terminals 20 and 22. To overcome the saturation of this amplifier by the relatively large stimulation pulse, fast recovery switches 44 are coupled to the amplifier 42 and to the constant current driver 12. The fast recovery switches act to eliminate, within 8 milliseconds after the stimulus, any electrical charges which remain on various capacitive components within the various amplifier units and current drivers.

Referring to FIG. 2, lines 2-A to T, a timing diagram for use in conjunction with FIG. 1, the stimulus signals $P_{ST}$ and ST (FIG. 2, line 2-A) occur at periodic intervals, assuming the absence of spontaneous cardiac activity. The stimulus signal is ST, a pulse of approximately 0.5 millisecond duration, and is reshaped into a shorter 0.1 millisecond duration signal $P_{ST}$ by amplifier 208 (FIG. 5). The response of the heart, (FIG. 2, line 2-B), normally comprised of a depolarization potential D and a repolarization potential R, as distinct from the spontaneous "R-wave", occurs thereafter. The saturation of the amplifier unit 26, as indicated by the signal at FIG. 2, line 2-C, at the output of delay 32, holds the pacer refractory for the blocking interval. If the pacer is in its DEMAND mode, the presence of a spontaneous R-wave, FIG. 2, line 2-D, in FIG. 2, providing it occurs after the end of the pacer refractory period but before the end of the stimulus release interval T (measured from the prior stimulus) will reset the generator 10. The next stimulus pulse ST, FIG. 2, line 2-A ($A_1$), thus cannot occur until the end of the predetermined time period T. It is apparent that if the rate of occurrence of spontaneous activity continues to exceed the intrinsic pacer rate (1/T), no stimuli will be released, i.e., pacer activity is suppressed and the pacer remains in its "standby" condition. p On the assumption that pacer stimuli are not thus suppressed, the stimulus pulse ST will be applied to the timing circuit of FIG. 5 (explained in further detail below) to generate a series of timed signals. The ST signal is reshaped by amplifier 208 to generate the $P_{ST}$ signal. The first of these timing signals, $P_R$, FIG. 2, line 2-F, will be applied after a delay determined only by the width of the $P_{ST}$ pulse, to the fast recovery switch 44, thereby unblocking the amplifier system 26 and the drivers 12. The unblocking is effective within the duration of the $P_R$ pulse (8 milliseconds). The differential amplifier 42 is thus able to pass (or detect) the response, FIG. 2, line 2-B or FIG. 2, line 2-E, providing that it occurs 8 milliseconds or more after ST has terminated.

Two sampling tests are shown in FIG. 1. These tests are made to indicate the occurrence of an adequate response by the heart to the pacer stimulus ST. The two components of this response (D and R, FIG. 2, line 2-B) are tested individually. The $SP_A$ pulse serves to test the depolarizing response D, the second $SP_B$ pulse is used to test the repolarizing response R. The signals $SP_A$ and $SP_B$ are supplied from the circuit of FIG. 5 and occur at times set by delay elements 200 and 202, respectively. These times are determined by observation of the total response (FIG. 2, line 2-B) at the output of amplifier 42 and are set so that $SP_A$ occurs at the peak of the D response and $SP_B$ occurs at the peak of the R response. The depolarizing test is effected through a coincidence gate 46, while the repolarizing test is effected through a logic coincidence gate 48. The signal levels are appropriately signed such that the presence of the response signals during the sampling periods will produce an appropriate gated output signal to the amplifier 52. In practice, the gates are actually individual dual input FET circuits whose outputs are directly tied together, (constituting a logical buffer) and connected to the input of amplifier 52. The presence of an $SP_A$ and $SP_B$ signal acts to open the respective gate 46, 48 and permits the passage of the signal amplitude from the amplifier 42.

It is noted that although testing of both depolarization and repolarization signals is shown, it is often simpler and more convenient to perform the sampling test solely on the depolarizing signal, since the depolarization response is generally larger and more stable. It is possible, however, to test the repolarization signal alone, or to use both tests for greater reliability.

The outputs of the gates 46 and 48, representing the magnitudes of the sampled signals, are fed to an amplifier 52. The gain of the amplifier 52 is set to provide a safety factor with respect to the minimum amplitudes to be permitted for the R and D responses. These minimum amplitudes are defined by the threshold controls (plus and minus) on comparator elements 56 and 58 which are discussed further below. The normal gain setting (safety factor) is such that it provides a signal amplitude to the amplitude comparators which is, preferably, between 2 and 3 times the selected threshold levels. The output of amplifier 52 is supplied to a comparator stage 54. The comparator stage includes threshold adjustments which are matched to the patients R and D cardiac responses to pacer stimuli ST. These responses may vary for each individual, and it is thus preferable, although not essential, to appropriately set these threshold controls at the time of pacer installation. Thus, the gain of both amplifier 52 and the threshold levels of the comparator stage 54 act in conjunction to provide appropriate comparator outputs, FIG. 2, line 2-L. When the signals at the output of amplifier 52 (FIG. 2, line 2-K) do not reach threshold (points $K_1$ and $K_2$, FIG. 2, line 2-K), no corresponding output will emerge from the comparator stage 54. As shown, the comparator stage 54 includes a positive (+) comparator 56 and a negative (−) comparator 58 which are used as previously discussed. Comparator stage 54 is designed such that any voltage more negative or more positive than the corresponding threshold voltage selected, gives rise to constant, unipolar (positive) pulse outputs whose duration is that of either $SP_A$ or $SP_B$. It thus functions to measure the absolute value (ABV) of the R and D responses.

The outputs of the comparator stage 54 are amplified in amplifier 60 to provide the absolute value signals ABV for subsequent processing. The absence of an ABV signal (cf: FIG. 2, lines 2-K and 2-L) will indicate a failure of the comparator stage 54 input signal to meet either of its preset R and D threshold levels, an event defined as "loss of capture".

The pacer of the present invention is designed to sense a plurality of loss of capture events before instituting corrective and warning action. To this end, the invention employs a loss of capture detection monitor illustrated generally in FIG. 3 and including therein an N stage counter 62 coupled to a $2^N$ line decoder 64, which acts to decode the output of the N stages counter 62 to a one out of Y signal, where $Y=2^N$. For example, if a three stage binary counter (N=3) is employed, then the decoder 64 will have $Y=2^N$ or 8 output lines, as shown. The counter and decoder are conventional components.

A control flip-flop 66 is coupled to a specific output of the decoder 64, in accordance with the desired and preset number of loss of capture events which will ultimately provide corrective and warning signals. The flip-flop 66 is of conventional design, and in the illustration given (FIG. 3), has its set input coupled to the fourth line of the decoder through a buffer (OR) gate 68, by a selector switch 70. In the implantable model of this pacer, switch 70 is replaced by a permanent connection to a selected value chosen by the surgeon. An external pacer of this design will retain the selector switch. It should be noted that the first line of the decoder is numbered to "0" but it represents a valid counter condition (001 in a three stage binary counter) and a 1 event condition. Thus, the fourth line is numbered "3" representing four events, with the fourth event giving rise to an output to flip-flop 66. Greater or lesser event conditions can be set by adjustment of the switch 70, in the external unit, or by presetting a permanent connection in the internal unit.

Figure 3:
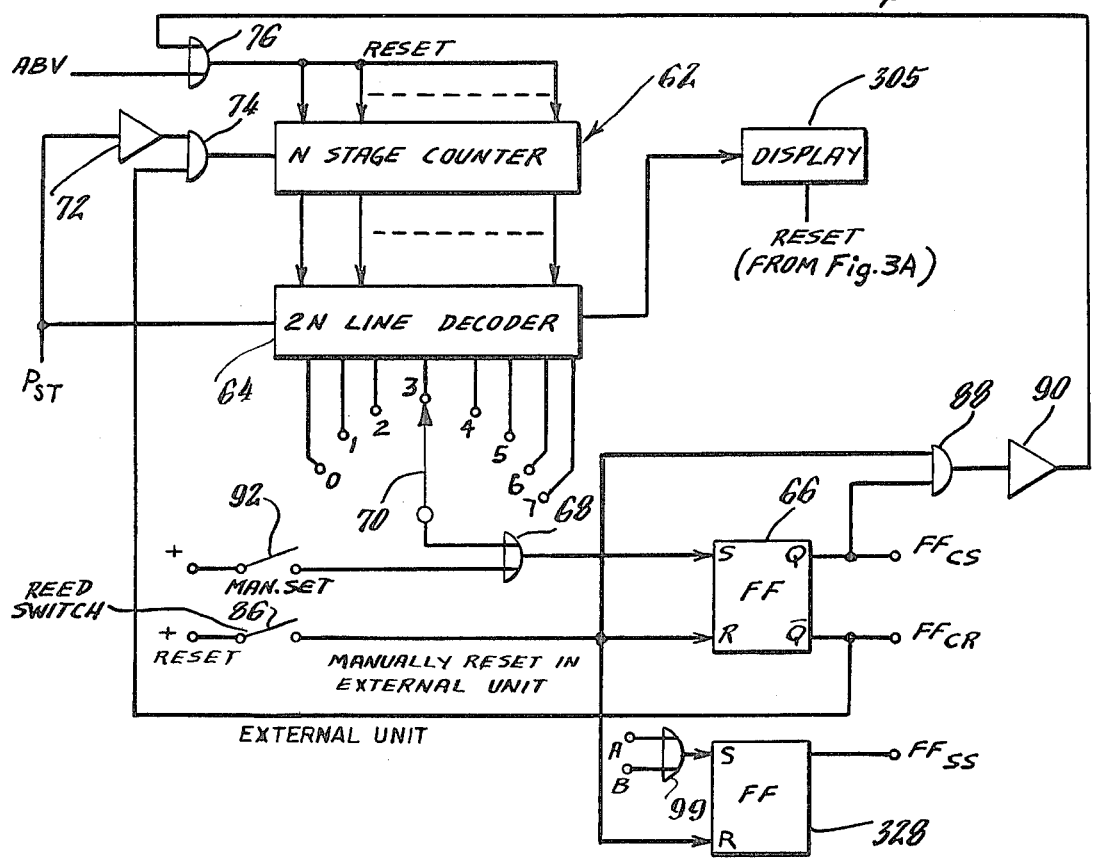
FIG. 3 is a block diagram of the external monitoring logic employed in conjunction with FIG. 1.
Figure 3A:
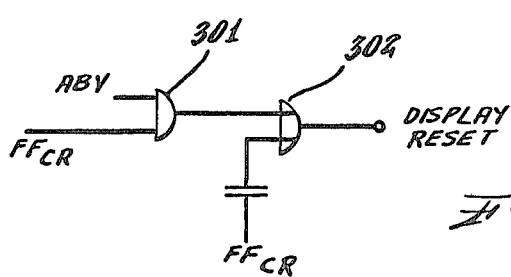
FIG. 3A is a detail of the display reset circuitry.
Figure 3B:
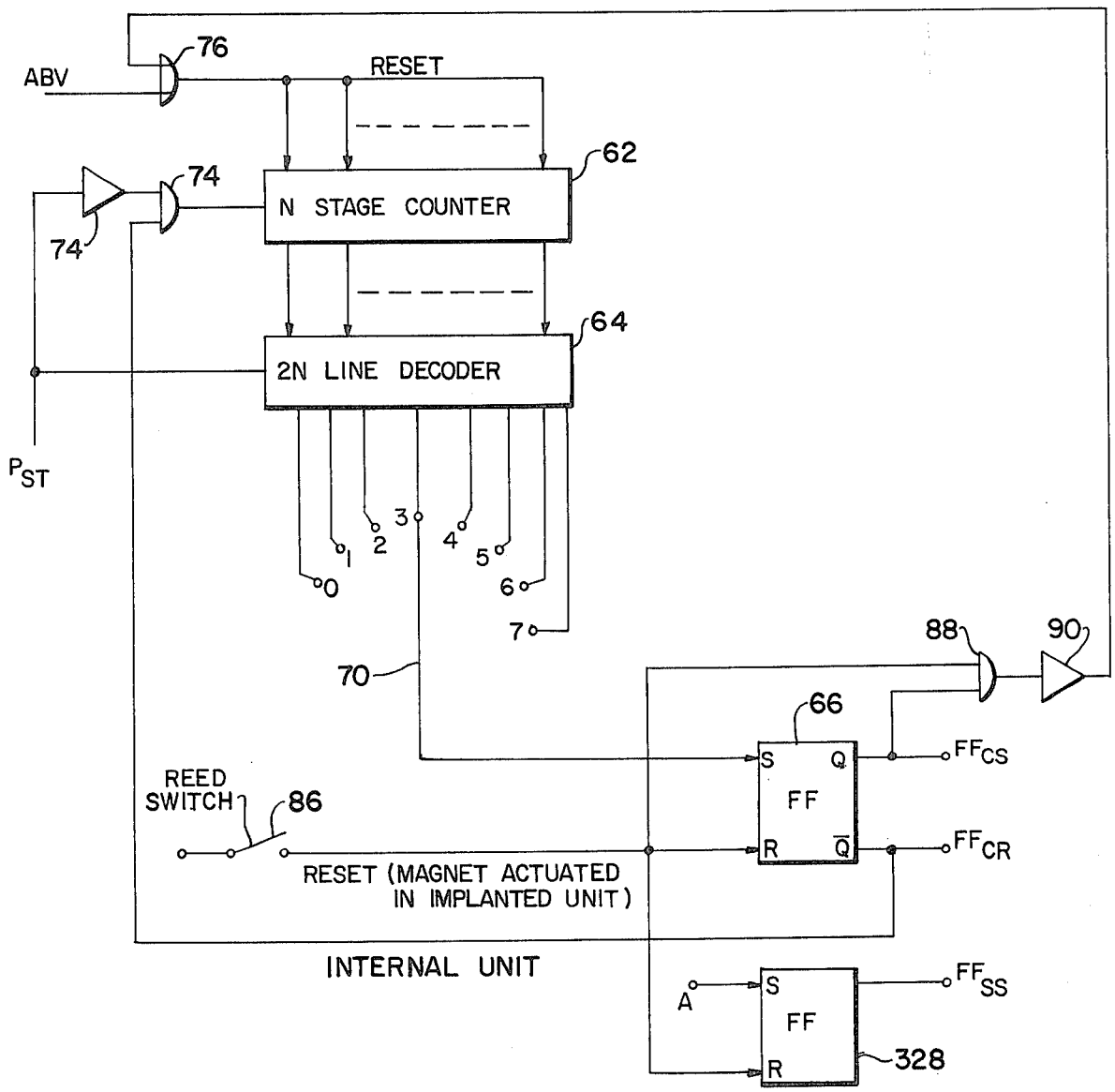
FIG. 3B is a block diagram of the implanted monitoring logic employed in conjunction with FIG. 1.

The operation of the detection monitors of FIGS. 3 and 3B will now be set forth. Corresponding reference numbers indicate corresponding components. The stimulus pulse $P_{ST}$ derived from the signal ST, will activate amplifier 72 and thus enter the counter 62 through the coincidence (AND) gate 74, and accumulate one count, (FIG. 2, line 2-$M_1$). The gate 74 will have had its other input preconditioned by virtue of the normal state of flip-flop 66 providing a "high" output is present on output line $FF_{CR}$. Immediately thereafter, should the comparator stage 54 pass a signal exceeding the selected threshold values an ABV signal will be generated. The ABV signal will enter the buffer (OR) gate 76 and reset the counter 62. Should the ABV signal not occur, the counter 62 will not be reset. Thus, if the counter 62 remains set after the threshold tests have been made at the times determined by delay elements 200 and 202, such a set condition indicates the absence of an adequate R or D response to ST, i.e., "loss of capture." An identical test is made to test the heart's response to the next ST. This second ST pulse will cause counter 62 to accumulate a second count, and initiate the events which enable the next test. If this test indicates that either the R or D signals are above the selected threshold, an ABV signal is generated and counter 62 is reset to zero. Thus, the line "3" output of counter 62 decoder 64 is activated by a fourth indication of "loss of capture" providing that there have been three previous, consecutive, failures. For ease of illustration, FIG. 2 presumes the switch position to have been set at position "1". Thus, referring to FIGS. 2 and 3, assuming that both the R and D responses to the first stimulus exceed the selected threshold, the counter will be reset to zero at the time of occurrence of the $SP_A$ pulse. If a second stimulus evokes a subthreshold R response but an adequate D response, the counter will be reset to zero at the time of occurrence of the $SP_B$ pulse. In neither of these situations has there been "loss of capture". As illustrated, the third stimulus fails to evoke either an adequate R or D response. Thus an ABV signal is absent, and the first counter stage is set (FIG. 2, line 2-M). Assuming now that the next stimulus again fails to capture, the ABV signal is again absent. Thus the counter accumulates the count of 2, with the first stage being reset by the second $P_{ST}$, causing the second stage to set (FIG. 2, lines 2-$M_1$ and 2-$M_2$). An output pulse thus appears on line "1" coincident with the next $P_{ST}$, FIG. 2, line 2-N). This pulse will be applied through switch 70, via buffer gate 68, to the flip-flop 66, causing the output $FF_{CS}$ to go high (FIG. 2, line 2-0) and $FF_{CR}$ to go low. Gate 74 is thus blocked from further count pulses and the counter 62 stage 2 holds this condition until reset, as described further below.

As a consequence of the setting of flip-flop 66, several actions transpire. As shown in FIG. 2, line 2-I, an alarm signal $ST_{2C}$ generated by elements 204 and 205 of the timing circuit of FIG. 5 is provided. $ST_{2C}$ occurs at a time set by 204 and has a fixed duration (2 milliseconds). Referring to FIG. 1, the setting of flip-flop 66 output $FF_{CS}$ to a higher state places a high signal on line 78, thereby energizing the ST pulse doubling circuit 80. The pulse doubling circuit 80 is coupled to the constant current driver 12 and increases the level of the stimulation signal ST, FIG. 2, line 2-A, point $A_2$. Although the term "doubler" is used, it is understood that an increase in magnitude of the stimulating signal ST is intended, and that a range of increased magnitudes may be chosen, of which doubling is the preferred. Increasing the magnitude of the stimulating pulse in this manner provides a high probability for regaining capture. At the same time, the high signal on line 78 provides a conditioning signal to the coincident (AND) gate 82, thereby permitting the pulse input circuit 84 to inject an additional alarm signal $ST_{2C}$ into the driver 12. As a result, the pacer now provides a supplemental signal displaced from the principal stimulation signal ST. This signal (FIG. 2, line 2-S, FIG. 2, line 2-A, point $A_3$) may be seen by a clinician on a standard electrocardiographic recording, and will continue to be present until the counter 62 and flip-flop 66 are reset as discussed below. Thus, a permanent record is maintained of a loss of capture event, whereas such an event would have previously gone unreported in prior art devices. Thus, the unit is not only self-correcting, but diagnostic as well. The use of the increased magnitude signal would not normally be sufficient by itself as a diagnostic indicator because of the variations in recorded amplitude as a function of electrode position with respect to the heart. The supplemental alarm pulse, however, is a time distinguishing event, and clearly indicatable on EKG recording equipment. The pulse $ST_{2C}$ is set to occur in the "absolute refractory period" of the heart following the doubled stimulus. The usual absolute refractory period of a human heart is normally about 50–70 milliseconds, and any stimuli occurring in that interval following an adequate ST will be ineffective. $ST_{2C}$, set to occur during this period, will therefore serve only as a warning or alarm pulse. Its width is set at 2 milliseconds so as to make it more readily visible on the EKG recording.

After EKG checking by the clinician, the counter 62 and flip-flop 66 are resettable by external actuation in FIG. 3 by momentarily closing the manual reset switch 86. In an implanted pacer, switch 86 is embodied as a magnetic reed switch which can be actuated by an RF generator which is brought near to the switch activating the RF detector 395 and driver element 396, causing the closure of switch 86. As a result, a momentary signal, FIG. 2, line 2-Q, is applied to coincident (AND) gate 88, the reset input to flip-flop 66, amplifier 90 and buffer (OR) gate 76, thus resetting the counter 62. In the external pacers, of FIG. 3 the $FF_{CR}$ output is also applied to buffer gate 302 with an ABV pulse to coincidence gate 301 as shown in FIG. 20. The output of gate 301 is applied through a buffer (OR) gate 302, along with a differential FFCR pulse, to reset a visible display 305 of the state of the to reset a visible display 305 of the state of counter 62. The flip-flop 66 also changes state, FIG. 2, line 0, rendering $FF_{CS}$ low and $FF_{CR}$ high. Thus, the counter 62 is enabled for beginning its count sequence again, and the doubling and warning circuits 80 and 84, respectively, are disabled.

Figure 4:
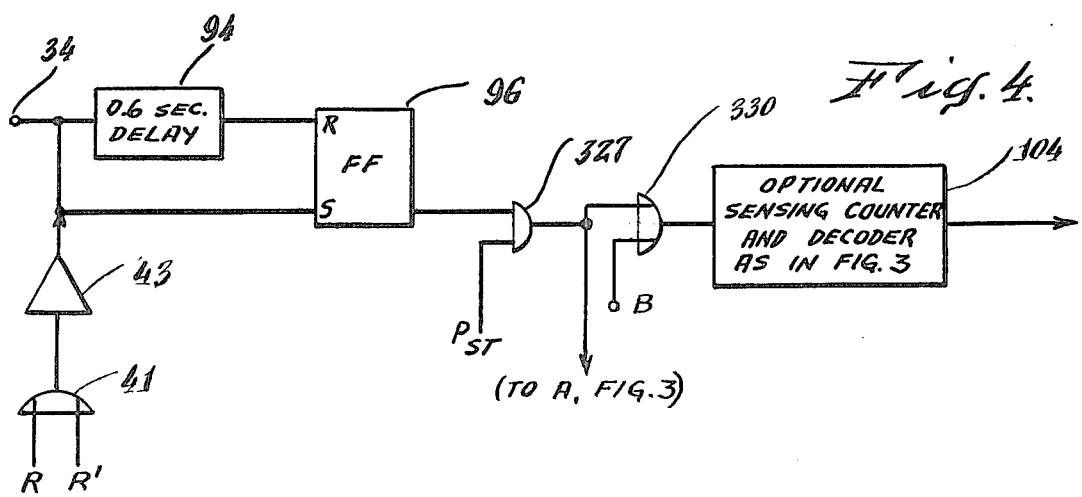
FIG. 4 is a further set of monitoring logic employed for detecting sensing failures.

One other form of failure detection which is designed into the pacer of the present invention is the detection of sensing failure. This condition occurs when the pacer releases a stimulus at a time when the occurrence of spontaneous activity should have supressed it. This type of failure is detected in the manner illustrated generally in FIG. 4. It is assumed that spontaneous activity occurs at some time between (a) the end of the refractory period of the heart following an adequate stimulus, and (b) the release of the next ST at the end of interval T (the reciprocal of the pacer's intrinsic rate). This spontaneous activity generates a signal R on line 34 or R' on line 39A from gate 39. R, as noted previously, is generated if spontaneous activity occurs during the non-refractory period of amplifier 26. R' is a conditioned output derived from the essentially non-refractory amplifier 42. Thus, the spontaneous activity which also appears at the input to 42 gives rise to a signal at the output of 42. This signal is applied to gate 37 together with an RINH. signal derived from the 0.25 second monostable multivibrator 208A (FIG. 5). The effect of RINH. is to block outputs from 42 for 0.25 seconds after the stimulus ST. Thus, R' is necessarily coincident with R, and is in effect a redundant R signal. If one of these signals is absent due to component failure, the other is likely to be present, since the probability of coincident failure is low R and R' are buffered together through buffer gate 41 (FIG. 4). The output of gate 41 is amplified by amplifier 43, whose output is used to set flip-flop 96, enabling coincidence gate 327. Gate 327 remains enabled for a period of 0.6 seconds, since the same spontaneous activity acts to reset flip-flop 96 via the 0.6 second delay element 94. If an ST pulse is generated within this 0.6 second interval, a sensing failure has occurred, since the normal pacemaker rate is normally not set to exceed 90 beats per minute, corresponding to an escape interval T=0.67 seconds. (An ST pulse would normally not have occurred prior to the end of this minimum escape interval following a spontaneous R wave). Thus, if a sensing failure does occur and the ST pulse is incorrectly released a $P_{ST}$ pulse passes through gate 327, providing signal A. Flip-flop 328 is set by the signal A, and remains set until reset by the action of switch 86 (as previously described). The flip-flop 328 set output ($FF_{SS}$, FIG. 2, line 2-R) conditions the coincident (AND) gate 98 to allow passage of the timed SF marker pulse, FIG. 2, line 2-J, provided from the timing circuit of FIG. 5. The SF marker pulse is timed so as to occur sufficiently displaced from the stimulus signal ST and warning signal $ST_{2C}$ so as to be distinguishable therefrom, and shown at point $A_4$ on FIG. 2, line 2-A. The coincidence of the two signals at gate 98 passes a pulse to the sensing failure pulsing circuit 100 which energizes the constant current driver 12 to place the signal, FIG. 2, line 2-T, on the output terminals 20 and 22, in the manner described heretofore in connection with the warning signal $ST_{2C}$. Thus, a sensing failure pulse will also be established on the EKG trace. The sensing failure may be permanently established, notwithstanding recovery of sensing, until manually or clinically reset, as was done in connection with the loss of capture warning signal $ST_{2C}$. Further, a counting/decoding system, equivalent to that employed in FIG. 3, may also be employed in FIG. 4, to establish a sensing failure condition only after a predetermined number of failures have occurred.

The ST signal can also be employed along with the output of flip-flop 96 to count predetermined numbers of sensing failures in appropriate circuitry, shown generally, but corresponding to that employed in FIG. 3 or 3B. The sensing failure signal SF as supplied by the drivers 12 is sufficiently narrow in width (0.1 millisecond or less) so as to not exhibit any stimulating characteristics.

Referring to FIG. 5, a timing circuit is shown for generating each of the above discussed wave forms in timed relationship. Each spaced signal is generated from the original ST signal from the generator 12, coupled via amplifier 208 and appropriately delayed by delays 200, 202, 204, 206, 209. The pulse width time durations are determined by the conventional monostable multivibrators 201, 203, 205, 207, 208A and 210, employed to generate the pulses used throughout the system. These pulses are $P_R$ (recovery pulse), $SP_A$ (depolarizing sample pulse), $SP_B$ (repolarizing sample pulse), $ST_{2C}$ (capture failure alarm pulse) and SF (sensing failure alarm pulse).

It may also be noted that if a sensing failure occurs, simultaneous indication of loss of capture may also be displayed if the uninhibited stimulus ST occurs within the total (absolute plus relative) refractory period of the heart (about 100 to 250 milliseconds) which follows the occurrence of spontaneous activity. In such an event, the ST pulse initiates the usual loss of capture test, and since the R and D responses may not be evoked during this refractory period, loss of capture may also be indicated.

Figure 6:
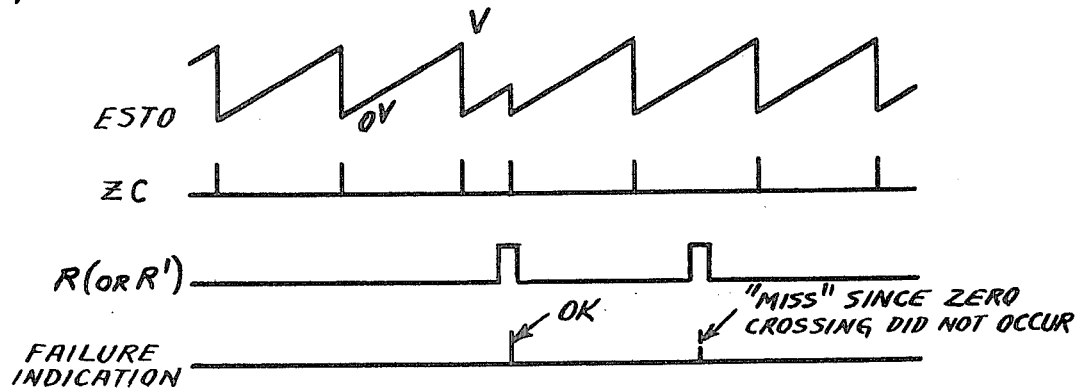
FIG. 6 shows an implementation of the present invention for detecting a sensing failure.
Figure 7:
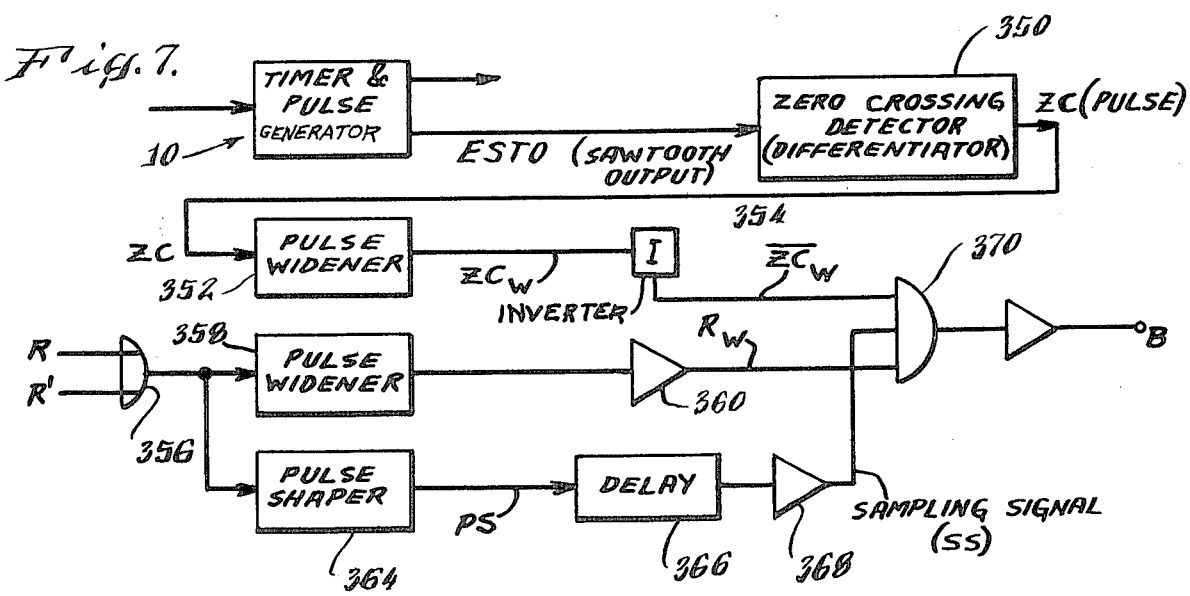
FIG. 7 is a logic circuit illustrating the implementation of the method of FIG. 6.
Figure 8:
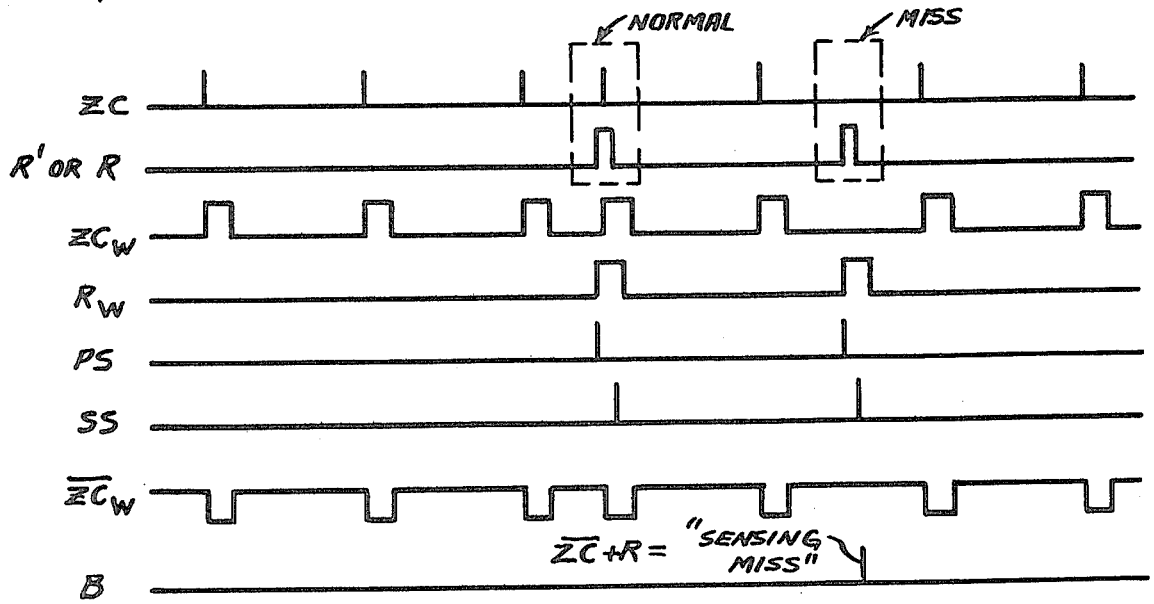
FIG. 8 is a timing diagram illustrating the relationship of the components described in FIG. 7.

The alternate method and apparatus of detecting a sensing failure which is the particular subject to which this invention is directed is illustrated in FIGS. 6-8. This method makes use of the essential property of the pacer pulse generator and timer in its relation to the R-wave — i.e., that since the R-wave must recycle the timer, a voltage change across a "timing capacity" within the timer must be observed in a specific time relation to the R-wave. If this voltage change does not occur, a sensing failure must follow. Thus, as illustrated; the ZC (zero crossing) output in FIG. 6, represents wherein the voltage ESTO across the timing capacitance is shown as the saw-tooth wave form emerging from timing generator 10. For each zero crossing thereof, a ZC pulse is generated. The R'-R-wave timing is shown below the ZC signals.

The occurrence of an R-wave and the simultaneous absence of ZC means that the timing circuit has not been properly recycled. The output B is used in a manner identical to that described above to initiate the counting and marking of sensing failures. As before, the R-wave makes use of the redundant amplifiers in the pacer, R and R'. Logically, only $(R + \overline{ZC})$ = sensing "miss." All of the other possibilities $(\overline{R} + \overline{ZC})$, $(\overline{R} + ZC)$ and $(\overline{R} + ZC)$ are permitted.

The circuit for logical implementation of the method illustrated by FIG. 6 is shown in FIG. 7, and the timing relationship of such components in FIG. 8.

Referring to FIG. 7, the timer and pulse generating circuit 10 (See FIG. 1) produces a saw-tooth output signal ESTO (FIG. 6) which is applied to a zero crossing detector 350, producing the ZC pulse (See FIG. 8). The Zc pulse is applied to the pulse widener 352 and to the inverter 354 to produce $\overline{ZCw}$.

The signals R or R' (SeeFIG. 1) are applied through the OR gate buffer 356, pulse widener 358 and isolation amplifier 360 to produce the Rw signal. The output of 356 goes to pulse shaper 364 to provide the signal PS to delay 366 and isolation amplifier 368, thereby providing a sampling signal SS.

The signals $\overline{ZCw}$ and Rw are sampled by signal SS in gate 370 to provide the logic signal ($\overline{ZCw}$ + Rw), indicating a sensing failure, B.

The sensing failure signals A and B, (FIG. 5) can be injected through OR gate buffer 330 directly into the optional counter as well as being introduced through or gate buffer 99 to set the sensing failure indicator FF 328 (FIG. 3). Thus, a "miss" is detected as the absence of recycling (zero crossing) following the occurrence of an R-wave (B), or by the premature release of a stimulus following an R-wave (A).

Thus, an autodiagnostic pacer, operating in either fixed mode or demand mode, has been described with the advantages of sensing loss of capture and failure, and providing increased magnitude stimulating signals (to correct loss of capture) and appropriate warning signals which may be permanently maintained, even after the event has corrected itself.

In the external unit, the pacer may be provided with various features enabling the clinician to make adjustments. Typical of these are the gain controls symbolized by circles with arrows therein which are coupled to various units shown in the figures. These controls, while not normally present in the implantable units, may exist therein in the form of miniature components which may be permanently adjusted to each patient by the attending physician or surgeon prior to implant.

It will be understood that although various preferred time durations for pulses and signals have been set forth, they are intended to be exemplary only and not limiting. Variations in timing will be apparent to those skilled in the art within the ambit of the inventive scope.

While the invention has been disclosed with reference to a limited number of embodiments, it will be apparent that variations and modifications may be made therein, and it is intended in the following claims to cover each such variation and modification as falls within the true spirit and scope of the invention.

What is claimed is:

1. An improvement for detection of a sensing failure in a pacer for cardiac pacing and condition monitoring, including generating means for providing periodic cardiac stimulating signals over a predetermined time period, sensing means responsive to cardiac activity for providing an electrical signal in accordance with said cardiac activity, comparing means for comparing a threshold signal level to said electrical signal, and monitoring means providing a first output signal for changing the electrical characteristics of the signals provided by said generating means by a first amount sufficient to be discernible when said comparing means indicates that said electrical signal did not exceed said threshold level, said sensing means responsive to each spontaneous cardiac event for resetting said generating means to the initial level of said predetermined time period, the improvement comprising means for providing a first signal corresponding to each said initial level, means for providing a second signal in accordance with each said spontaneous cardiac event, means for coincidently comparing said first and second signals, means for generating a second output signal in response to said first and second signals not coinciding, said lack of coincidence indicating a sensing failure, and means responsive to said second output signal for changing the electrical characteristics of the signals provided by said generating means by a second amount sufficient to be discernible.

2. The pacer of claim 1, wherein said first output signal represents a loss of capture, and said monitoring means includes means for increasing the magnitude of said cardiac stimulating signal in response to said output signal from said monitoring means for effecting recapture, and said second output signal represents a sensing failure, said monitoring means including means coupling said second output signal thereto to provide a warning signal from said generating means indicative thereof.

3. The pacer of claim 1, wherein said monitoring means includes means for generating a warning signal in spaced time displacement relative to each said cardiac stimulation signal, in response to each of said output signals from said monitoring means, said warning signals each time displaceably discernible on said electrocardiogram.

4. An improvement for detection of a sensing failure in a pacer for cardiac pacing and condition monitoring, including generating means for providing periodic cardiac stimulating signals over a predetermined time period, sensing means responsive to cardiac activity for providing an electrical signal in accordance with said cardiac activity, comparing means for comparing a threshold signal level to said electrical signal, and monitoring means providing a first output signal for changing the electrical characteristics of the signals provided by said generating means by a first amount sufficient to be discernible when said comparing means indicates that said electrical signal did not exceed said threshold level, said sensing means responsive to each spontaneous cardiac event for resetting said generating means to the initial level of said predetermined time period, the improvement comprising a zero crossing detector coupled to the output of said generating means, said generating means providing a saw tooth wave form output with a period equal to said predtermined time period, said zero crossing detector providing a first signal with each initiation of said saw tooth wave, gating means, first and second source means each for providing a second signal corresponding to a spontaneous cardiac event, said gating means responsive to a coincidence between said first and second signals for producing a second output signal, said second output signal representative of a sensing failure, and means responsive to said second output signal for changing the electrical characteristics of the signals provided by said generating means by a second amount sufficient to be discernible.

5. The pacer of claim 4, wherein said first output signal represents a loss of capture, and said monitoring means includes means for increasing the magnitude of said cardiac stimulating signal in response to said output signal from said monitoring means for effecting recapture, and said second output signal represents a sensing failure, said monitoring means including means to provide a warning signal from said generating means indicative thereof.

6. The pacer of claim 4, wherein said monitoring means includes means for generating a warning signal in spaced time displacement relative to each said cardiac stimulation signal, in response to each of said output signals from said monitoring means, said warning signals each time displaceably discernible on said electrocardiogram.

7. In a method for detection of a sensing failure in a pacer for cardiac pacing and condition monitoring, including the steps of generating periodic cardiac stimulating signals over a predetermined time period, sensing cardiac activity for providing an electrical signal in accordance with said cardiac activity, comparing a threshold signal level to said electrical signal, providing a first output signal for changing the electrical characteristics of said stimulation signals by a first amount sufficient to be discernible when said comparing step indicates that said electrical signal did not exceed said threshold level, said sensing each spontaneous cardiac event for resetting said stimulation signals to the initial level of predetermined time period, the improvement comprising the steps of providing a first signal corresponding to each said stimulation signal, providing a second signal in accordance with each said spontaneous cardiac event, coincidently comparing said first and second signals, generating a second output signal in response to said first and second signals not coinciding, said lack of coincidence indicating a sensing failure, and changing the electrical characteristics of said stimulation signals by a second amount sufficient to be discernible in response to said second output signal.

* * * * *